United States Patent [19]

Petrtyl et al.

[11] Patent Number: 4,743,263

[45] Date of Patent: May 10, 1988

[54] ADAPTABLE ISOELASTIC HIP-ENDOPROSTHESIS

[75] Inventors: Miroslav Petrtyl; Rudolf Pavlansky; Jaroslav Valenta, all of Prague, Czechoslovakia

[73] Assignee: Ceske vysoke uceni technicke, Prague, Czechoslovakia

[21] Appl. No.: 779,655

[22] Filed: Sep. 24, 1985

[30] Foreign Application Priority Data

Nov. 9, 1984 [CS] Czechoslovakia .................... 8553-84

[51] Int. Cl.⁴ .............................................. A61F 2/32
[52] U.S. Cl. .......................................... 623/23; 623/16
[58] Field of Search ....................... 623/16, 17, 18, 19, 623/20, 21, 22, 23; 128/92 YZ

[56] References Cited

U.S. PATENT DOCUMENTS

| | | | |
|---|---|---|---|
| 4,266,302 | 5/1981 | Tornier | 623/22 |
| 4,445,579 | 5/1984 | Inamori et al. | 108/92 ZY |
| 4,457,301 | 7/1984 | Walker | 128/212 YZ |
| 4,516,277 | 5/1985 | Butel | 623/23 |

FOREIGN PATENT DOCUMENTS

| | | | |
|---|---|---|---|
| 2475892 | 8/1981 | France | 623/23 |
| 0581938 | 11/1977 | U.S.S.R. | 623/16 |

Primary Examiner—Richard J. Apley
Assistant Examiner—David J. Isabella

[57] ABSTRACT

Adaptable isoelastic hip endoprosthesis comprising a joint piece connected to a shaft of the endoprosthesis which shaft is to be implanted in the femur, said shaft being composed of at least two spirally twisted elastic rods. Such rods can be of the same cross section, can have a variable cross section, and can have the same or different lengths.

3 Claims, 2 Drawing Sheets

ADAPTABLE ISOELASTIC HIP-ENDOPROSTHESIS

This application is related to application Ser. No. 676,573, and to companion application S 10606.

BACKGROUND OF THE INVENTION

The invention relates to an adaptable isoelastic hip endoprosthesis.

An actually used hip endoprosthesis which is implanted in the femur with the use of bone cement comprises either a stiff shaft or a shaft composed of a system of straight rods which are mutually connected and thus form a stiff statically indeterminate system of statically overdetermined shape, which has no possibility to adapt itself to the shape of the cavity of the femur.

SUMMARY OF THE INVENTION

It is an object of this invention to provide a hip endoprosthesis which is isoelastic and adaptable to the shape of the cavity created for the prosthesis in the femur. The adaptable isoelastic hip endoprosthesis according to this invention comprises a substantially spherical joint part with a stem, which stem is composed of at least two elastic rods twisted in spiral shape. These spirally twisted elastic rods can be of unequal length, and may also have a variable cross section. They can advantageously be mutually connected on their lower ends. Furthermore, they can also be provided on their lower ends with stabilization bodies.

In the case in which the endoprosthesis according to this invention is implanted in a cavity of the femur, a prestress in the radial direction is created, and the rods adjust themselves to the anatomical shape of the marrow channel, so that the required stabilization of the endoprosthesis in the femur is achieved. After the scar of the implant has healed, a perfect elastic unit is thus created. The negative influences of bone cement from the biomechanical and biological point of view are thereby eliminated, whereby the bone marrow need not be removed. An advantage of the arrangement according to this invention is also that the spongious bone part remains and serves as regeneration material.

DESCRIPTION OF THE DRAWINGS

The object of this invention and its effects will be described in following in more detail with respect to the examplary embodiments shown in the attached drawings, in which.

DESCRIPTION OF PREFERRED EMBODIMENTS

Figure 1:
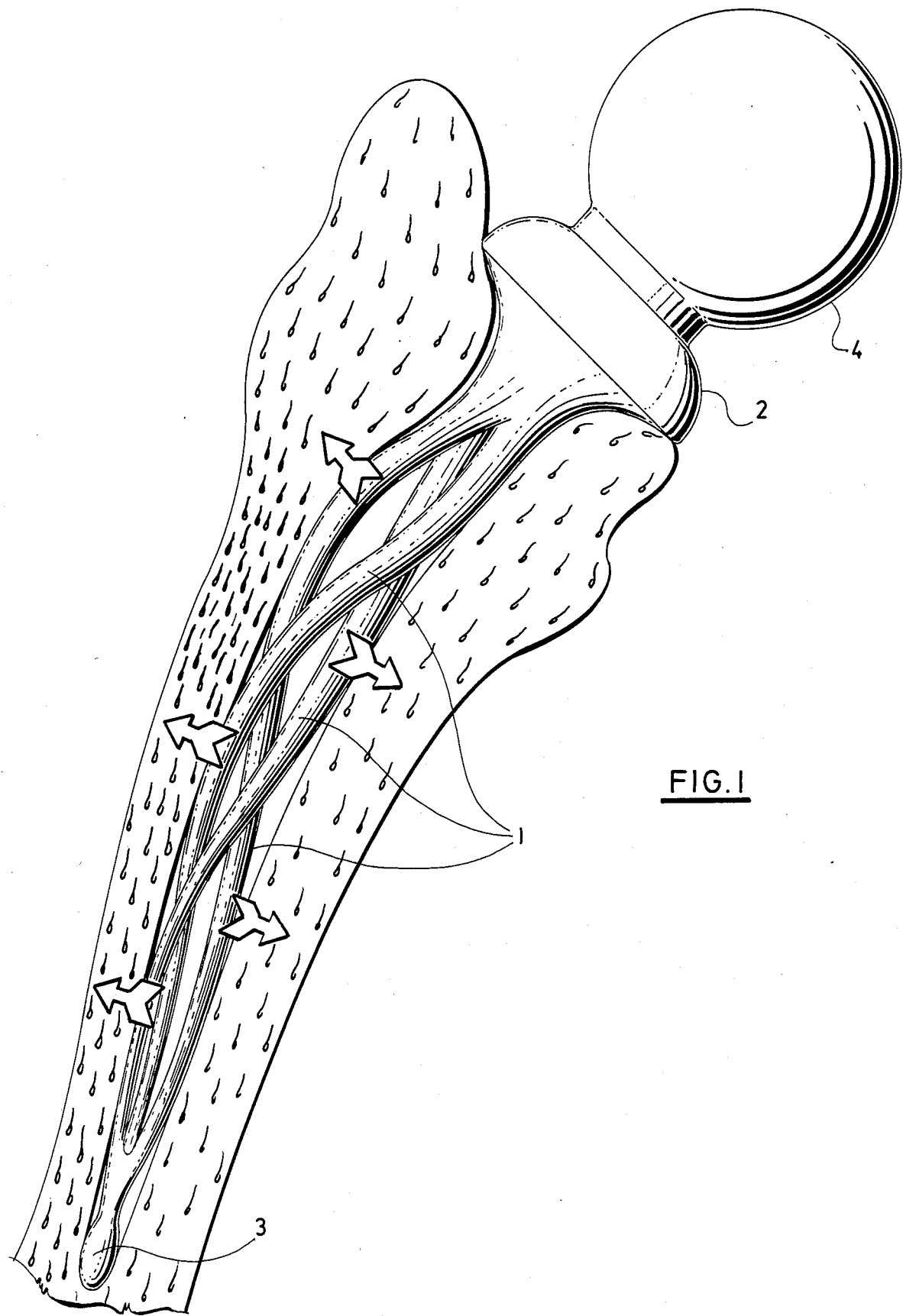
FIG. 1 is an overall view of an adaptable isoelastic hip endoprosthesis according to this invention with spirally twisted elastic rods of the stem connected at their lower ends.

With reference to FIG. 1, the shaft of the endoprosthesis is composed of two or more elastic rods 1 spirally twisted in a left or a right hand direction, with a circular, elliptic, rectangular, or other suitable cross section, said rods 1 being fixed at their upper ends to a flange 2 and with their lower ends mutually firmly connected. The bundle of spirally twisted elastic rods 1 has a diameter of a turn larger than the diameter of the cavity of the femur at the same part of cross section perpendicular to the longitudinal axis of the shaft of the implant. Thus, a prestress in the radial direction is generated after the introduction of the elastic implant into the cavity of the femur, and the required stabilization of the endoprosthesis is achieved. After the corresponding scar has healed, a perfect elastic unit with the implant is achieved.

Figure 2:
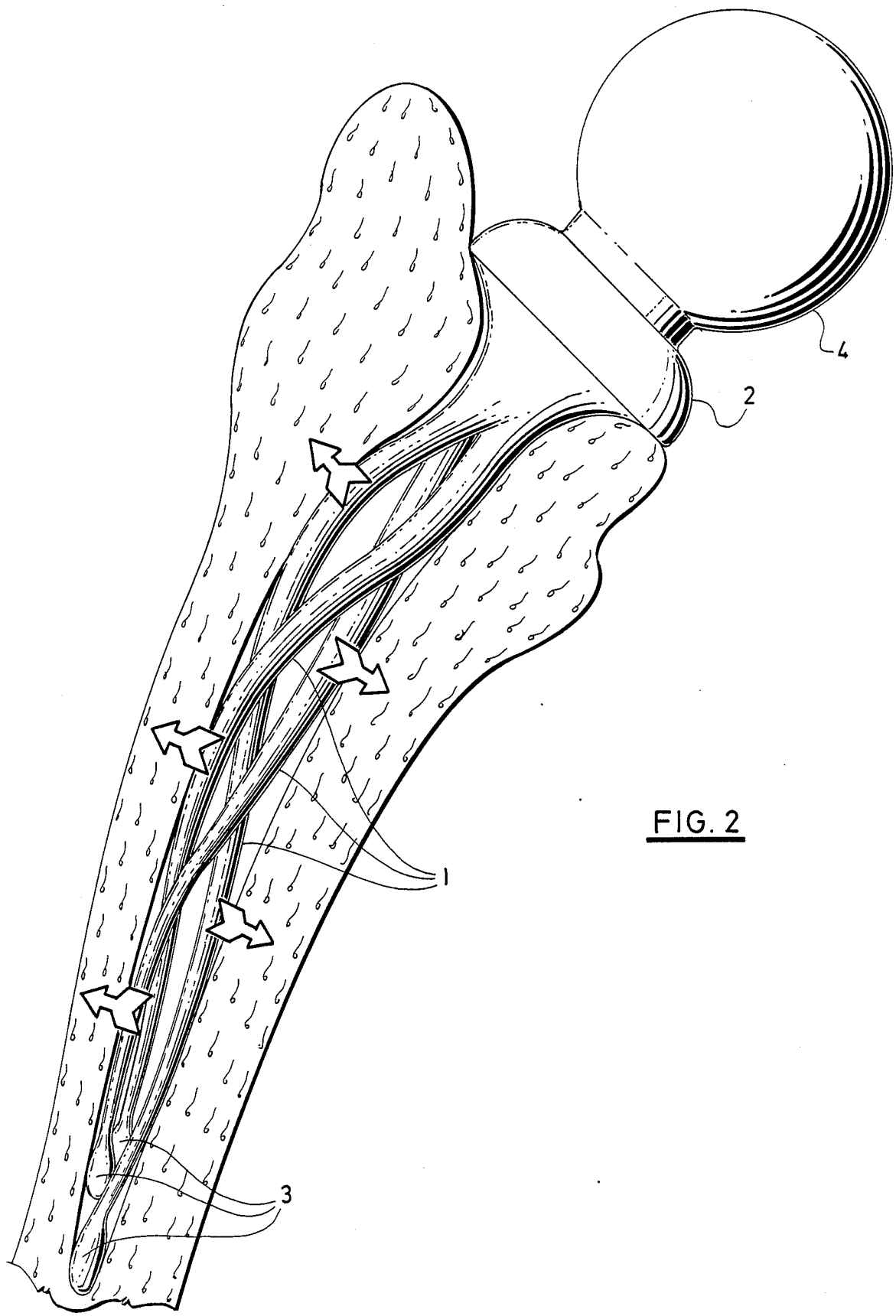
FIG. 2 is a similar view with free lower ends of spirally twisted rods of the stem.

The endoprosthesis according to FIG. 2 also comprises two or more elastic rods 1 twisted in the right or left hand direction, rods 1 being of circular, elliptical, rectangular, or other suitable cross section adapted to be introduced into the marrow cavity of the femur, into which the spirally twisted elastic rods 1 extend and bear on the internal surface of the corticalis. Due to the thus generated radial stress of the spirally twisted rods, a stabilization of the shaft of the implant is achieved; the spirally twisted elastic rods 1 of the shaft adjust themselves to the anatomical shape of the marrow channel. After the respective scar has healed, a perfect functional unit with implant is achieved.

The spirally twisted elastic rods 1 of the endoprosthesis according to FIG. 2 are provided at their lower ends with stabilization bodies 3 forming with each spirally twisted elastic rod 1 a unit or which are connected therewith by welding or by some other known method. The stabilization bodies 3 have the shape of an oval, a drop, a ball, or a plate. The contact surfaces of the spirally twisted elastic rods 1 with the corticalis are either smooth or are made rough by fine droplets in order to obtain an optimum fixation. The opening for introduction of the implant into the cavity of the femur is prepared in advance by means of a special known tool.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. Adaptable isoelastic hip endoprosthesis for insertion into a prepared cavity comprising a joint part connected to a shaft of the endoprosthesis, said shaft of the endoprosthesis being composed of at least two spirally twisted elastic rods having a turn larger than the diameter of said cavity whereby upon insertion of said shaft into said cavity prestresses said elastic rods in a radial direction thereby allowing said rods to adjust to the anatomical shape of said cavity; wherein the spirally twisted elastic rods have a variable cross section and are provided at their lower end with stabilization bodies.

2. Adaptable isoelastic hip endoprosthesis for insertion into a prepared cavity comprising a joint part connected to a shaft of the endoprosthesis, said shaft of the endoprosthesis being composed of at least two spirally twisted elastic rods having a turn larger than the diameter of said cavity whereby upon insertion of said shaft into said cavity prestresses said elastic rods in a radial direction thereby allowing said rods to adjust to the anatomical shape of said cavity; wherein the spirally twisted elastic rods have a variable cross section, are of unequal length, and are provided at their lower end with stabilization bodies.

3. Adaptable isoelastic hip endoprosthesis comprising a joint part connected to a shaft of the endoprosthesis for insertion into a prepared cavity, said shaft of the endoprosthesis being composed of at least two spirally twisted elastic rods having a turn larger than the diameter of said cavity whereby upon insertion of said shaft into said cavity prestresses said elastic rods in a radial direction thereby allowing said rods to adjust to the anatomical shape of said cavity; wherein the spirally twisted elastic rods have a variable cross section, are of unequal length, and are provided at their lower end with stabilization bodies and are firmly connected at said lower ends.

* * * * *